United States Patent [19]

Krabbenhoft

[11] 4,366,089

[45] Dec. 28, 1982

[54] CALCIUM-NICKEL PHOSPHATE CATALYST

[75] Inventor: Herman O. Krabbenhoft, Scotia, N.Y.

[73] Assignee: General Electric Company, Schenectady, N.Y.

[21] Appl. No.: 260,873

[22] Filed: May 6, 1981

[51] Int. Cl.³ .................... B01J 27/14; B01J 31/02
[52] U.S. Cl. ........................ 252/437; 252/428
[58] Field of Search ................. 252/428, 437

[56] References Cited

U.S. PATENT DOCUMENTS

| | | | |
|---|---|---|---|
| 2,442,320 | 5/1948 | Britton et al. | 585/631 |
| 2,816,081 | 12/1957 | Heath et al. | 252/448 X |
| 2,824,843 | 2/1958 | Dietzler et al. | 585/632 X |
| 2,971,035 | 2/1961 | Stringer et al. | 585/412 |
| 3,396,205 | 8/1968 | Alexander et al. | 252/437 X |
| 3,420,887 | 1/1969 | Noddings et al. | 252/437 X |
| 3,542,813 | 11/1970 | Jeger et al. | 260/343.42 |
| 3,595,808 | 7/1971 | Bertsch et al. | 252/437 |
| 3,625,647 | 12/1971 | Stowe | 252/437 X |
| 3,935,126 | 1/1976 | Vrieland | 585/441 X |

OTHER PUBLICATIONS

A Calcium-Niphosphate Dehydrogenation Cat., Britton et al., Industrial and Engineering Chem., vol. 43, No. 12, pp. 2871-2874.

*Primary Examiner*—Delbert E. Gantz
*Assistant Examiner*—William G. Wright
*Attorney, Agent, or Firm*—Joseph T. Cohen; James C. Davis, Jr.

[57] ABSTRACT

The life of a calcium-nickel phosphate catalyst used for dehydrogenation purposes can be increased by treating the catalyst with a mixture of air, phenol, water, and isopropylphenol at elevated temperatures.

6 Claims, No Drawings

IMPROVED CALCIUM-NICKEL PHOSPHATE CATALYST

This invention is concerned with increasing the life of a calcium-nickel phosphate catalyst. More particularly, the invention relates to a method for improving the life of a calcium-nickel phosphate catalyst (hereinafter referred to generically as "catalyst") used in the dehydrogenation of para-isopropylphenol to para-isopropenylphenol, which process comprises contacting the catalyst at temperatures of about 550°–650° C. with a feed composed of phenol, water, and para-isopropylphenol.

In my copending application, Ser. No. 252,653, filed Apr. 9, 1981 now U.S. Pat. No. 4,346,249 and assigned to the same assignee as the present invention, is disclosed and claimed a process for making para-isopropenylphenol from para-isopropylphenol by dehydrogenating the latter in the presence of a calcium-nickel phosphate catalyst. The para-isopropenylphenol thus formed has many uses, particularly in the synthesis of 2,2-bis-(para-hydroxyphenyl) propane, also known as "bisphenol-A" used to make various resins, as a comonomer for polymerizing with other olefinic materials such as the copolymerization of para-isopropenylphenol with styrene, methyl methacrylate, etc., and as an antioxidant.

As described in my aforementioned patent application, the calcium-nickel phosphate catalyst, although effective as a dehydrogenation catalyst, has some shortcomings in that the life of the catalyst is often curtailed as a result of carrying out the dehydrogenation reaction. As further pointed out in the aforesaid patent application, the activity of the catalyst can be regenerated by heating the latter at an elevated temperature of about 800° C. for several hours after which the dehydrogenation reaction can be carried out for an additional amount of time before the catalyst again showed signs of inactivity.

I have now discovered that this calcium-nickel phosphate catalyst can be treated in such a manner that when used for dehydrogenation of the para-isopropylphenol to the para-isopropenylphenol, its activity as a catalyst can be significantly increased to a point where the need for reactivation by heating at elevated temperatures is significantly reduced and may even be eliminated. In accordance with my invention, prior to use of the catalyst with the para-isopropylphenol (hereinafter identified as "propylphenol"), the catalyst is treated with a feed composed of phenol, water, and the para-isopropylphenol with air at a temperature ranging from about 550°–650° C., after which air alone is passed through the catalyst and then the treated catalyst can then be employed for its intended purpose at a lower temperature of reaction.

The "calcium nickel phosphate catalyst" a specific example of which is one having the formula:

$$Ca_8Ni(PO_4)_6 \qquad \text{I}$$

can be prepared in various ways. Normally, the catalyst comprises a normal metal phosphate material consisting of phosphate radicals chemically combined with calcium and nickel in a molar ratio of calcium of from 6.5 to 12, preferably from 7.5 to 9.2, atoms of calcium per atom of nickel, the total amount of calcium and nickel being sufficient to satisfy the valences of the phosphate radical. One method is to form a mixture of calcium and nickel salts with a water-soluble ortho-phosphate whereby the calcium nickel phosphate is formed as a suspension of small particles. Methods for preparing the catalyst may be found, for instance, in U.S. Pat. No. 3,542,813 issued Feb. 20, 1951; U.S. Pat. No. 2,816,081 issued Dec. 10, 1957, U.S. Pat. No. 2,442,320 issued May 25, 1948; U.S. Pat. No. 2,824,843 issued Feb. 25, 1957; U.S. Pat. No. 3,935,126 issued Jan. 27, 1976; U.S. Pat. No. 2,971,035 issued Feb. 7, 1961; and in the article in *Industrial and Engineering Chemistry,* 43, 2871-2874—Britton et al. published December, 1951. By reference, these patents and article are made part of the disclosures and teachings of the instant application as means for describing and making the calcium-nickel phosphate catalyst.

In the practice of my invention for improving the life of the catalyst, the catalyst is packed into a reaction tube, usually a quartz reaction tube, normally used for carrying out the dehydrogenation reaction and thereafter the feed comprising the phenol, water, air, and para-isopropylphenol is passed through the catalyst at a temperature of between 550°–650° C. and preferably between 560°–630° C. Advantageously thereafter, the passage of air is maintained through the catalyst bed within essentially the same temperature range for a period of from 2 to 20 hours, after which the catalyst is ready to be used for dehydrogenating the para-isopropenylphenol (hereinafter identified as "propenylphenol").

Generally, the feedstock used to give added life to the catalyst is essentially the same kind of feedstock which is used in the dehydrogenation step, except that it is done on a preliminary basis in order to enhance the life of the catalyst.

It was entirely unexpected and in no way could have been predicted that the preliminary passage of a feedstock through the catalyst at elevated temperatures before proceeding with the actual dehydrogenation step would enhance the life of the catalyst. Thus, if the dehydrogenation is continued with the feedstock, without the preliminary step comprising the essence of the presently claimed invention, the life of the catalyst is reduced as is more particularly brought out in my aforesaid copending patent application.

The amount of water used with the propylphenol is not critical and can be varied widely. Thus, for each mol of para-isopropylphenol employed in the feed, one can use from 0.5 to 5 mols of phenol and from 0.5 to 4 mols of the water. Simultaneously, with the passage of the feed, air is also passed through the catalyst bed. I have found that at an air feed of about 0.1 to 0.5 ft.$^3$/hr., when combined with the liquid feedstock (that is the phenol, water, and para-isopropylphenol) is adequate for producing a catalyst which has an exceptionally long life. After the catalyst has been treated for life improvement, the para-isopropylphenol can then be dehydrogenated in the same fashion as that disclosed and claimed in my aforementioned copending application.

In order that those skilled in the art may better understand how the present invention may be practiced the following examples are given by way of illustration and not by way of limitation. Unless otherwise indicated, all parts are by weight.

The apparatus used for treating the catalyst through which ultimately the para-isopropylphenol will be passed for dehydrogenation purposes, consisted of a quartz tube 40 centimeters × 16 millimeters, inside diameter, with Vigreux indentations one inch above the top to the bottom joint. This tube is packed with 3 cm of quartz rings and 28 cm (equivalent to 44.16 grams) of the calcium-nickel phosphate catalyst of formula I which had previously been calcined at about 800° C. for a period of about 17 hours to remove any materials used in the preparation of the catalyst, such as graphite, employed to facilitate pelletizing the catalyst for its intended purposes. This calcining can take place for a period of time ranging from 5–20 hours. The tube was then filled with additional quartz rings for heat transfer. Thermocouples were placed on the side of the tube and the tube placed in a vertical furnace. At the top of the tube was placed a manifold from which the air and liquid feeds were added, including later the ultimate feed comprising the para-isopropylphenol being dehydrogenated. At the bottom of the tube were placed in series three, three-necked flasks, the first two being immersed in ice/water baths.

EXAMPLE 1

Using the apparatus described above, the catalyst bed was heated to about 560°–630° C. with an air flow of 0.5 ft.$^3$/hr. Thereafter, a liquid feed composed of phenol, water, and para-isopropylphenol in a molar ratio of 2.8:2.1:1.0 was introduced (while continuing to pass the air) to provide an addition rate of liquid feed of about 0.15 ml/min. After about 6 hours, the flow of feed was discontinued, at which point HNMR and HPLC analyses indicated that virtually all of the isopropylphenol had been consumed and that the product was composed mostly of phenol and unidentified materials and none of the expected para-isopropenylphenol. The air flow was continued for an additional 17 hours at the same temperature, 560°–630° C. Thereafter, the temperature was lowered to 370°–440° C. and the flow of the same above-described feed with air was initiated to make para-isopropenylphenol. After specified volumes of feed had been introduced, the products were collected from the receiver and analyzed for para-isopropenylphenol content by HNMR spectroscopy. A total of 42 cuts were taken giving a total volume of about 375 ml. Analysis indicated that conversion of the isopropylphenol to the isopropenylphenol was between about 30–35%.

When the above test was carried out similarly with the exception that the catalyst was not pretreated in the manner described above, it was found that the catalyst became inactive after the passage of about 50 to 60 ml of the feed. Although it could be demonstrated, as described in my aforementioned patent application, that the activity of the catalyst could be regenerated by heating the catalyst at about 800° C., Example 1 above shows a marked increase in catalyst life by at least a factor of six was achieved thus predicting possible continuous conversion to the para-isopropenylphenol as a result of pretreatment of the catalyst to increase its life. Although the test was discontinued after about 40 hours, there was reason to believe that had the passage of the feed over the pretreated catalyst continued, the life and activity of the catalyst would have remained essentially the same for an indefinite period of time.

EXAMPLE 2

In this example, the procedure employed in Example 1 was repeated by passage of the mixture of air, phenol, water, and para-isopropylphenol over the pretreated catalyst, this time at a temperature of about 400°–480° C. for 37 hours. A total of 23 cuts were taken yielding a total volume of about 330 ml product whose conversions to the para-isopropenylphenol were between about 25–30%.

The results of Examples 1 and 2 should be contrasted with the results obtained using a similar calcium-nickel phosphate catalyst which has not been pretreated wherein after specified liquid feed volumes were introduced, activity of the catalyst went down, and even though the rate of conversion may have been somewhat higher, the activity of the catalyst diminished so that it needed reactivation by the high temperature treatment at about 800° C. after a relatively short period of time (about 7 hrs.).

It will of course be apparent to those skilled in the art that in addition to the conditions employed in the above-identified example, other conditions and proportions of ingredients, time of reaction, temperatures, etc., within the parameters previously recited, may be used within the scope of the claimed invention.

What I claim as new and desire to secure by Letters Patent of the United States is:

1. A method for improving the life of a calcium-nickel phosphate catalyst used in the dehydrogenation of para-isopropylphenol to para-isopropenylphenol, which process comprises passing through the calcium-nickel phosphate catalyst at a temperature of 550°–650° C., air first and then both air and a feed composed of phenol, water, and para-isopropylphenol, discontinuing the passage of this feed and continuing passage of air through the catalyst prior to its first use as a dehydrogenation catalyst.

2. The process as in claim 1 wherein the air is at a feed rate of about 0.1 to 0.5 ft.$^3$/hr.

3. The process as in claim 1 wherein the temperature at which the feed is passed through the catalyst ranges from about 560°–630° C.

4. The process as in claim 1 wherein the air flow is continued for a period of from 2 to 20 hours after cessation of passage of the feed.

5. The process as in claim 1 wherein the calcium-nickel phosphate catalyst has the formula:

$$Ca_8Ni(PO_4)_6.$$

6. The method as in claim 1 where the ingredients in the liquid feed are in a molar ratio of 0.5 to 5 mols phenol to 0.5 to 4 mols water per mol para-isopropylphenol.

* * * * *